(12) United States Patent
Sumida et al.

(10) Patent No.: US 9,469,863 B2
(45) Date of Patent: Oct. 18, 2016

(54) AMINOGLYCOSIDE ANTIBIOTICS, PROCESS FOR PRODUCING THE SAME, AND PHARMACEUTICAL USE THEREOF

(75) Inventors: Naomi Sumida, Odawara (JP); Koji Yanai, Minamiashigara (JP); Masato Tani, Kawasaki (JP); Takayoshi Fukushima, Odawara (JP); Yasumasa Ota, Odawara (JP); Shuichi Gomi, Tokyo-To (JP); Akitaka Nakane, Kawasaki (JP)

(73) Assignee: MEIJI SEIKA KAISHA, LTD., Tokyo-To (JP)

( * ) Notice: Subject to any disclaimer, the term of this patent is extended or adjusted under 35 U.S.C. 154(b) by 0 days.

(21) Appl. No.: 12/734,848

(22) PCT Filed: Dec. 1, 2008

(86) PCT No.: PCT/JP2008/071795
§ 371 (c)(1),
(2), (4) Date: Jun. 14, 2010

(87) PCT Pub. No.: WO2009/069800
PCT Pub. Date: Jun. 4, 2009

(65) Prior Publication Data
US 2011/0034405 A1 Feb. 10, 2011

(30) Foreign Application Priority Data
Nov. 30, 2007 (JP) .................................. 2007-310618

(51) Int. Cl.
*C07H 15/234* (2006.01)
*C12P 19/48* (2006.01)
*A61K 31/7036* (2006.01)
*C12R 1/465* (2006.01)

(52) U.S. Cl.
CPC .......... *C12P 19/485* (2013.01); *A61K 31/7036* (2013.01); *C07H 15/234* (2013.01); *C12R 1/465* (2013.01)

(58) Field of Classification Search
USPC .............................................. 536/13.7, 13.8
See application file for complete search history.

(56) References Cited

FOREIGN PATENT DOCUMENTS

| JP | H02-117385 | 5/1990 |
| JP | 2003-61671 | 3/2003 |
| JP | 2004-173537 | 6/2004 |
| JP | 2006-296419 | 11/2006 |

OTHER PUBLICATIONS

International Preliminary Report on Patentability issued Aug. 19, 2010 in International (PCT) Application No. PCT/JP2008/071795.
International Search Report issued Feb. 10, 2009 in International (PCT) Application No. PCT/JP2008/071795.
M. Kojima et al., "Microbial Semi-Synthesis of Aminoglycosidic Antibiotics by Mutants of *S. ribosidificus* and *S. kanamyceticus*", The Journal of Antibiotics, vol. 26, No. 12, pp. 784-786, Dec. 1973.
T. Hirayama et al., "Role of Glutamate 243 in the Active Site of 2-Deoxy-Scyllo-Inosose Synthase from *Bacillus circulans*", Bioorganic & Medicinal Chemistry, vol. 15, No. 1, pp. 418-423, Jan. 2007.
M. K. Kharel et al., "Identification of 2-Deoxy-Scyllo-Inosose Synthase in Aminoglycoside Producer Streptomyces", Journal of Microbiology and Biotechnology, vol. 13, No. 5, pp. 828-831, 2003.
M. K. Kharel et al., "A Gene Cluster for Biosynthesis of Kanamycin from *Streptomyces kanamyceticus*: Comparison with Gentamicin Biosynthetic Gene Cluster", Archives of Biochemistry and Biophysics, vol. 429, No. 2, pp. 204-214, 2004.
F. Kudo et al., "Purification and Characterization of 2-Deoxy-Scyllo-Inosose Synthase Derived from *Bacillus circulans*. A Crucial Carbocyclization Enzyme in the Biosynthesis of 2-Deoxystreptamine-Containing Aminoglycoside Antibiotics", The Journal of Antibiotics, vol. 52, No. 2, pp. 81-88, Feb. 1999.
D. Borders et al., "Detection of Naturally Occurring Hybrimycin-Type Antibiotics by Mass Spectroscopy", The Journal of Antibiotics, vol. 35, No. 8, pp. 1107-1110, Aug. 1982.
N. Yamauchi et al., "Biochemical Studies on 2-Deoxy-Scyllo-Inosose, An Early Intermediate in the Biosynthesis of 2-Deoxystreptamine", The Journal of Antibiotics, vol. 46, No. 12, pp. 1916-1918, Dec. 1993.
Japanese Office Action, with English translation, mailed Jan. 11, 2013 in corresponding Japanese Patent Application No. 2009-543896.
Supplementary European Search Report issued Oct. 22, 2013 in European Application No. 08854513.2.

(Continued)

*Primary Examiner* — Eric Olson
(74) *Attorney, Agent, or Firm* — Wenderoth, Lind & Ponack, L.L.P.

(57) ABSTRACT

The present invention relates to novel aminoglycoside antibiotics, a process for producing the same, and pharmaceutical use thereof. More specifically, the present invention relates to compounds represented by formula (I), a process for producing the same, and use of the same as antimicrobial agents.

[Chemical formula 1]

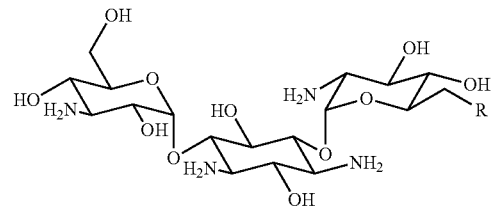

wherein R represents amino or hydroxyl.

13 Claims, No Drawings

(56) References Cited

OTHER PUBLICATIONS

A. Van Schepdael et al., "New Derivatives of Kanamycin B Obtained by Combined Modifications in Positions 1 and 6". Synthesis, Microbiological Properties, and In Vitro and Computer-Aided Toxicological Evaluation", Journal of Medicinal Chemistry, vol. 34, No. 4, pp. 1483-1492, Apr. 1, 1991.

Reconsideration Examination Report issued Aug. 19, 2015, in corresponding Japanese Application No. 2013-091738 with English translation.

Japanese Office Action dated Mar. 24, 2015 issued in corresponding Japanese Patent Applicaiton No. 2013-091738 (with English translation).

Japanese Office Action dated Sep. 2, 2014 issued in corresponding Japanese Patent Application No. 2013-091738 (with English translation).

AMINOGLYCOSIDE ANTIBIOTICS, PROCESS FOR PRODUCING THE SAME, AND PHARMACEUTICAL USE THEREOF

This application is a U.S. national stage of International Application No. PCT/JP2008/071795 filed Dec. 1, 2008.

CROSS-REFERENCE TO RELATED APPLICATIONS

This application is based upon and claims the benefit of priority from the prior Japanese Patent Application No. 310618/2007, filed on Nov. 30, 2007, the entire contents of which are incorporated herein by reference.

BACKGROUND OF THE INVENTION

The present invention relates to novel aminoglycoside antibiotics, a process for producing the same, and pharmaceutical use thereof.

BACKGROUND ART

Aminoglycoside antibiotics are a generic term for glycoside antibiotics containing amino sugar or aminocyclitol and exclude a group of antibiotics such as macrolides, nucleosides, and anthracyclines. Up to now, a number of aminoglycoside antibiotics have been discovered from culture of *actinomyces* or bacteria. Among them, streptomycin, neomycin, kanamycin, gentamicin, ribostamycin, tobramycin and the like have been used as useful chemotherapeutic agents. On the other hand, the widespread use of these aminoglycoside antibiotics in clinical practice has led to a problem of the appearance of bacteria resistant to aminoglycoside antibiotics.

Kanamycins (kanamycin A, kanamycin B, and kanamycin C) are aminoglycoside antibiotics produced by *Streptomyces kanamyceticus*. Kanamycins have a wide spectrum of antimicrobial activity. Since, however, many infecting bacteria become rapidly resistant to kenamycins, in recent years, the clinical adaptation of kanamycins is limited to diseases, mainly tuberculosis.

In kanamycins, kanamycin derivatives such as dibekacins, amicacins, and arbekacins effective also against resistant bacteria have been developed based on studies on a resistant mechanism. However, bacteria resistant to these agents are appearing. Under such circumstances, the development of novel aminoglycoside antibiotics that are effective against resistant bacteria and can reduce nephrotoxicity that is a problem common to aminoglycoside antibiotics has been expected.

Regarding aminoglycoside antibiotics comprising 2-deoxystreptamine as one constituent sugar, studies have been made on the production of novel aminoglycoside antibiotics by acquiring a mutant strain which produces an aminoglycoside antibiotic 2-deoxystreptamine-dependently, adding a 2-deoxystreptamine analog to the mutant strain, and cultivating the mixture. Also in kanamycins, there is a report that antibiotics different from kanamycins are produced by acquiring a mutant strain having a phenotype of 2-deoxystreptamine-dependent kanamycin production, adding 2-epistreptamine to the mutant strain, and cultivating the mixture (U.S. Pat. No. 3,669,838). Further, there is a report that 4-O-(α-D-glucopyranosyl)6-O-(3-amino-3-deoxy-α-D-glucopyranosyl)1-N-methyl-2-deoxystreptamine or 4-O-(α-D-glucopyranosyl)6-O-(3-amino-3-deoxy-α-D-glucopyranosyl)2-epi-streptamine is produced by adding 1-N-methyl-deoxystreptamine or myo-inosadiamine-1,3(2-epistreptamine) to a mutant strain having a phenotype of 2-deoxystreptamine-dependent kanamycin production and cultivating the mixture (Kojima, M. and Satoh, A., "Journal of Antibiotics", (Japan), 1973, Vol. 26, p. 784-786). Furthermore, there is a report that 4-O-(6-amino-6-deoxy-α-D-glucopyranosyl)6-O-(3-amino-3-deoxy-α-D-glucopyranosyl)streptamine (LL-BM27α) and 4-O-(6-amino-6-deoxy-α-D-glucopyranosyl)6-O-(α-D-glucopyranosyl)streptamine (LL-BM27β) are produced by adding streptamine to a mutant strain having a phenotype of 2-deoxystreptamine-dependent kanamycin production and cultivating the mixture (Borders, D. B. et al., "Journal of Antibiotics", (Japan), 1982, Vol. 35, p. 1107-1110). Here LL-BM27α is synonymous with 2-hydroxykanamycin A.

The amounts of aminoglycoside antibiotics produced by the addition of the substances and cultivation of the mixture are so small that the industrial applicability of the aminoglycoside antibiotics is low. Accordingly, it can be said that novel aminoglycoside antibiotics which are clinically useful and have potent antimicrobial activity are still demanded.

SUMMARY OF THE INVENTION

The present inventors have now found that novel aminoglycoside antibiotics having potent antimicrobial activity can be produced by cultivating a kanamycin producing strain derived from the genus *Streptomycin* together with a specific 2-deoxystreptamine analog. The present invention has been made based on such finding.

Accordingly, an object of the present invention is to provide novel aminoglycoside antibiotic agents possessing potent antimicrobial activity and a process for producing the same.

According to the present invention, there are provided aminoglycoside antibiotics that are compounds represented by formula (I) or their pharmacologically acceptable salts or their solvates.

[Chemical formula 1]

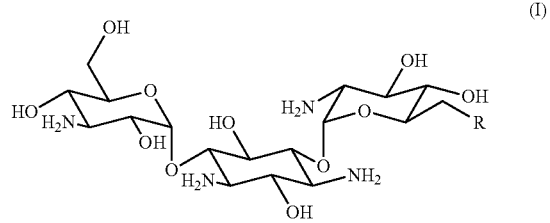

wherein R represents amino or hydroxyl.

According to another aspect of the present invention, there is provided a process for producing compounds represented by formula (I), the process comprising cultivating a kanamycin producing strain of the genus *Streptomyces* in a medium which comprises streptamine and/or myo-inositol to produce the compound.

The compounds according to the present invention have potent antimicrobial activity against bacteria causative of various infectious diseases and can be advantageously utilized in the treatment of infectious diseases. Further, the production process according to the present invention can simply and stably supply the above compounds.

DETAILED DESCRIPTION OF THE INVENTION

Deposit

The strain *S. Kanamyceticus*-DOS according to the present invention has been deposited with International Patent Organism Depositary, National Institute of Advanced Industrial Science and Technology (address: Tsukuba Central 6 Tsukuba-shi, Higashi 1-1-1, Ibaraki, 305-8566 Japan) (original deposited date: Nov. 1, 2007) under accession number FERM BP-11052.

DEFINITION

The term "2-hydroxykanamycin A" as used herein refers to a compound having hydroxyl introduced into the 2-position of kanamycin A. The term "2-hydroxykanamycin" refers to a group of compounds having hydroxyl introduced into the 2-position of kanamycins (kanamycin A, kanamycin B, and kanamycin C). Specifically, the group of compounds includes 2-hydroxykanamycin A, 2-hydroxykanamycin B, and 2-hydroxykanamycin C.

Further, the kanamycin producing strain, as used herein, which is "deoxystreptamine dependent" refers to a mutant strain, among kanamycin producing bacteria, that can restore the capability to produce kanamycins by adding deoxystreptamine.

The polypeptide "having activity functionally equivalent to" or "having functionally equivalent activity" as used herein refers to the following polypeptide.

In the polypeptide, in addition to polymorphisms or mutants of genes coding for the polypeptide, structural mutants may occur in an amino acid sequence, for example, by a modification reaction. However, it is known that some polypeptides, despite the presence of these mutants, have substantially the same physiological and biological activity as polypeptides not having a mutant. The polypeptide which, despite the structural difference, does not have a large difference in function refers to a polypeptide "having functionally equivalent activity."

Compounds Represented by Formula (I) or their Pharmacologically Acceptable Salts or Their Solvates One characteristic feature of the compounds represented by formula (I) according to the present invention is that hydroxyl has been introduced into the 2-position of kanamycin B or C. The compounds having the structure have a broad antimicrobial spectrum ranging from gram-positive bacteria to gram-negative bacteria including *Pseudomonas aeruginosa* and have potent antimicrobial activity.

According to one embodiment of the present invention, in the compounds represented by formula (I), R represents amino. This compound (hereinafter referred to as "hydroxykanamycin B") has a structure represented by formula (1).

[Chemical formula 2]

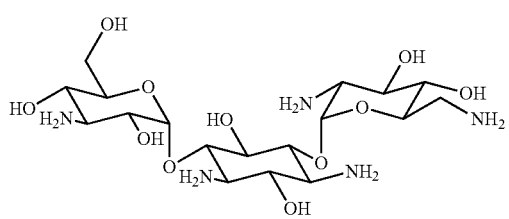

(1)

According to another embodiment of the present invention, in the compounds represented by formula (I), R represents hydroxyl. This compound (hereinafter referred to as "2-hydroxykanamycin C") has a structure represented by formula (2).

[Chemical formula 3]

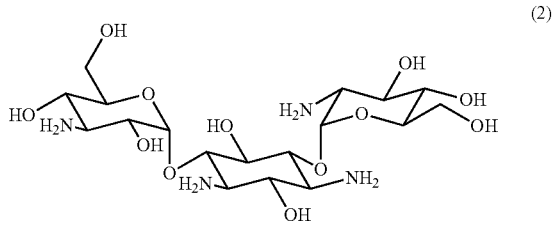

(2)

The compounds represented by formula (I) may be present as salts. Such salts include, for example, pharmaceutically acceptable salts. Specific examples thereof include hydrohalides such as hydrofluorides, hydrochlorides, hydrobromides, or hydroiodides, inorganic acid salts such as sulfates, phosphates, perchlorates, or carbonates, salts of carboxylic acids such as acetic acid, trichloroacetic acid, trifluoroacetic acid, hydroxyacetic acid, lactic acid, citric acid, tartaric acid, oxalic acid, benzoic acid, mandelic acid, butyric acid, maleic acid, propionic acid, formic acid, or malic acid, salts of amino acids such as alginic acid, aspartic acid, or glutamic acid, or salts of sulfonic acid such as methanesulfonic acid or p-toluenesulfonic acid. Preferred are hydrohalides such as hydrochlorides and inorganic acid salts such as sulfates.

The compounds represented by formula (I) or its pharmaceutically acceptable salts may exist as their solvates. Preferred solvates include hydrates, methanolates, or ethanolates.

Producing Strains

The compounds represented by formula (I) can be produced by various methods. For example, as described above, the compounds represented by formula (I) can be produced by cultivating a kanamycin producing strain of the genus *Streptomyces* in a medium comprising streptamine and/or myo-inositol.

Examples of such suitable producing strains include deoxystreptamine-dependent kanamycin producing strains. More preferred are strains of the genus *Streptomyces* wherein 2-deoxy-scyllo-inosose synthase catalyzing a first reaction in 2-deoxystreptamine biosynthesis from glucose-6-phosphoric acid has been inactivated. It is surprising that, when such strains are cultivated together with a deoxystreptamine analog, the compounds according to the present invention can be selectively produced without producing kanamycins.

Accordingly, according to still another aspect of the present invention, there is provided a kanamycin producing strain of the genus *Streptomyces* capable of producing compounds represented by formula (I) wherein 2-deoxy-scyllo-inosose synthase has been inactivated.

The mutant producing strain can be acquired, for example, by treating kanamycin producing bacteria which are derived from the genus *Streptomyces* including *Streptomyces kanamyceticus*, for example, by artificial mutation methods including ultraviolet (UV) irradiation or nitrosoguanidine (NTG). The acquisition of the desired mutant strain can be confirmed, for example, by acquiring a deoxystreptamine-dependent kanamycin producing strain, then measuring the activity of intracellular 2-deoxy-scyllo-inosose synthase in each mutant strain by a conventional method (Kudo, F. et al., "Journal of Antibiotics", (Japan), 1999, Vol. 52, p. 81-88), and selecting a mutant strain that does not have enzyme activity.

Regarding the kanamycin producing strain in which 2-deoxy-scyllo-inosose synthase has been inactivated, genes coding for 2-deoxy-scyllo-inosose synthase have already been clarified (Japanese Patent Application Laid-Open No. 173537/2004). Accordingly, a desired mutant strain can also be acquired by gene recombination technology. For example, a desired mutant strain may be acquired by destroying a gene coding for 2-deoxy-scyllo-inosose synthase. Further, the mutant strain can also be acquired by preparing a mutant gene having an amino acid substitution that provides inert 2-deoxy-scyllo-inosose synthase, and subjecting the mutant gene to gene substitution with a wild-type gene on a chromosome. The gene can be destroyed or substituted by methods commonly used in *Actinomyces* ("Practical *Streptomyces* Genetics", "The John Innes Foundation", (England), Norwick, 2000, p. 311-338). The disclosures of the document are incorporated herein by reference.

For example, a mutation in which aspartic acid at position 136 of the amino acid sequence of the synthase represented by SEQ ID No. 1 is substituted by asparagines may be mentioned as one example of mutation by which 2-deoxy-scyllo-inosose synthase is inactivated. Accordingly, the strain that can produce the compound represented by formula (I) can be acquired by integrating a gene coding a polypeptide having the mutation or a gene coding for an analog functionally equivalent to the polypeptide into a strain.

According to a preferred embodiment of the present invention, the kanamycin producing strain capable of producing the compound represented by formula (I) is the strain into which a gene coding for a polypeptide selected from the following polypeptides (a) to (c) has been integrated:

(a) a polypeptide consisting of an amino acid sequence represented by SEQ ID No. 1 having a mutation in which aspartic acid at position 136 has been changed to asparagine, (b) a polypeptide consisting of the amino acid sequence defined in (a) wherein one or more amino acids have been substituted, deleted, added, or inserted, the polypeptide having an activity functionally equivalent to the polypeptide defined in (a), and (c) a polypeptide consisting of an amino acid sequence having 80% or more homology with the amino acid sequence defined in (a), the polypeptide having an activity functionally equivalent to the polypeptide defined in (a)

*S. Kanamyceticus*-DOS may be mentioned as an example of suitable kanamycin producing strains corresponding to (a).

In (b), the "one or more amino acids" is preferably 1 to 40 amino acids, more preferably 1 to 8 amino acids, still more preferably 1 to 4 amino acids.

In (d), the homology is preferably not less than 90%, more preferably not less than 95%.

Further, when stable production of the compound represented by formula (I) is taken into consideration, preferably, the polypeptide described in (b) or (c) holds a mutation in which aspartic acid at position 136 in the amino acid sequence described in (a) or at a position corresponding to the position 136 has been changed to asparagine. The presence or absence of the mutation in the amino acid sequence described in (a) to (c) and the determination of sequence homology can be properly determined by a person having ordinary skill in the art by comparing the amino acid sequence represented by SEQ ID No. 1 with the amino acid sequence in (a) to (c) by a conventional method.

The functional equivalency between the polypeptide described in (b) or (c) and the polypeptide described in (a) can be confirmed by measuring 2-deoxy-scyllo-inosose synthase activity for both the polypepetides according to the above-described method described in Kudo, F. et al., "Journal of Antibiotics", (Japan), 1999, Vol. 52, p. 81-88 and comparing the measured results. Further, the functional equivalency can be indirectly confirmed by measuring the deoxystreptamine dependency or antimicrobial activity of kanamycin producing strain with genes coding for the polypeptides integrated thereinto by a method described in Example 2 or Test Example 1 and statistically comparing the measured results.

Production Process

As described above, the compound represented by formula (I) according to the present invention can be produced by cultivating a kanamycin producing strain derived from the genus *Streptomycin* in a medium which comprises a 2-deoxystreptamine analog selected from streptamine and myo-inositol.

When selective production of the compound represented by formula (I) is taken into consideration, as described above, the kanamycin producing strain derived from the genus *Streptomycin* is preferably a kanamycin producing strain in which 2-deoxy-scyllo-inosose synthase has been inactivated. However, a kanamycin producing strain in which 2-deoxy-scyllo-inosose synthase has not been inactivated may also be used. Examples of suitable strains in which 2-deoxy-scyllo-inosose synthase has not been inactived include *Streptomyces kanamyceticus*.

Further, in the production process according to the present invention, a combination of the kanamycin producing strain with the 2-deoxystreptamine analog added to the medium may be properly determined by taking the type of the desired contemplated compound into consideration.

According to one embodiment of the present invention, the kanamycin producing strain is one in which 2-deoxy-scyllo-inosose synthase has been inactivated, and the medium comprises streptamine. According to this embodiment, the compound represented by formula (I) can be produced together with 2-hydroxykanamycin A. This is advantageous in that 2-hydroxykanamycins (2-hydroxykanamycins A to C) can be simultaneously produced. Further, according to another embodiment of the present invention, the kanamycin producing strain is one in which 2-deoxy-scyllo-inosose synthase has been inactivated, and the medium comprises myo-inositol. According to this embodiment, 2-hydroxykanamycin C, which is a compound represented by formula (I) wherein R represents hydroxyl, can be selectively produced.

The addition amount of streptamine or myo-inositol may be properly varied depending upon cultivation conditions, but is preferably 100 to 50,000 μg/ml, more preferably 1,000 to 10,000 μg/ml.

Conventional substances may be properly added as ingredients of the medium in the production process according to the present invention.

Medium ingredients other than streptamine and myo-inositol usable herein include, for example, carbon sources such as glucose, sucrose, starch syrups, dextrins, starches, glycerol, syrups, animal and vegetable oils; and nitrogen sources such as soybean meals, wheat germ oils, corn steep liquors, cottonseed cakes, meat extracts, polypeptone, malt extracts, yeast extracts, ammonium sulfate, sodium nitrate, and urea. Further, if necessary, the addition of sodium, potassium, calcium, magnesium, cobalt, chlorine, phosphoric acid (for example, dipotassium hydrogenphosphate), sulfuric acid (for example, magnesium sulfate) and inorganic salts which can produce other ions is also effective. Furthermore, if necessary, various vitamins such as thiamines (for example, thiamine hydrochloride), glutamic acid (for example, sodium glutamate), amino acids such as asparagine (for example, DL-asparagine), micronutrients such as nucleotides, and selected drugs such as antibiotics may also be added. Furthermore, organic and inorganic substances that aid the growth of bacteria and promote the production of 2-hydroxykanamycin B and 2-hydroxykanamycin C can be properly added.

The medium is preferably approximately pH 5.5 to pH 9.

The cultivation may be carried out by solid cultivation, shaking cultivation, aeration agitation cultivation, or deep aerobic cultivation under aerobic conditions. Among them, the deep aerobic cultivation is preferred.

For example, 15° C. to 40° C. is suitable as the cultivation temperature. In many cases, however, bacteria are grown at a temperature around 25° C. to 35° C.

The amount of the compound represented by formula (I) produced varies depending upon the medium, cultivation conditions, and cultivation method used, but reaches the largest, for example, 2 days to 15 days.

Preferably, when the amount of the compound represented by formula (I) in the medium has reached the largest, the cultivation is stopped. The compound is then harvested from the culture and is purified.

In order to harvest the compound of the present invention from the culture, a conventional separation means utilizing the properties of the compound may be used. The separation means may be, for example, solvent extraction, ion exchange resin methods, adsorption or partition column chromatography, gel filtration, dialysis, precipitation, and crystallization, either alone or in an appropriate combination. For example, the culture is filtered to give a filtrate. The filtrate is then adsorbed on a cation exchange resin such as Amberlite IRC-50 or Amberlite FPC3500, and elution is carried out with aqueous ammonia. The eluate is further purified with a cation exchange resin such as Dowex 50W or Amberlite CG-50 and is if necessary purified by ion-exclusion chromatography with Dowex 1 or by adsorption chromatography with HP20ss, whereby each 2-hydroxykanamycin represented by formula (I) can be isolated.

Use

The compounds according to the present invention have potent antimicrobial activity and are useful for administration as a medicines to animals including human. Thus, according to a further aspect of the present invention, there is provided a pharmaceutical composition comprising a compound represented by formula (I) or its pharmacologically acceptable salt or their solvates. The composition is preferably used as an antimicrobial agent.

According to another aspect of the present invention, there is provided use of a compound represented by formula (I) or its pharmacologically acceptable salt or their solvates, in the manufacture of a pharmaceutical composition. According to still another aspect of the present invention, there is provided use of a compound represented by formula (I) or its pharmacologically acceptable salt or their solvates, in the manufacture of an antimicrobial agent.

When the compound according to the present invention is used as a pharmaceutical composition, the pharmaceutical composition may be formulated according to various dosage forms or usage forms by conventional methods. Pharmaceutical preparations for oral administration include tablets, pills, granules, capsules, powders, liquid formulations, suspensions, syrups, and sublingual agents. Pharmaceutical preparations for parenteral administration include injections, transdermal agents, inhalants, and suppositories. Pharmaceutical additives such as surfactants, excipients, stabilizers, wetting agents, disintegrants, dissolution aids, tonicity adjusting agents, buffers, colorants, and flavoring agents are properly used in the formulation.

Pharmaceutically acceptable carriers may be used as the carrier for the pharmaceutical composition. The type and composition of the carrier may be properly determined according to administration routes and administration methods. For example, liquid carriers usable herein include water, alcohols, soybean oils, and sesame oils. Example of solid carriers include sugars such as maltose and sucrose, amino acid salts such as lysine, polysaccharides such as cyclodextrin, organic acid salts such as magnesium stearate, and cellulose derivates such as hydroxylpropyl cellulose.

The compounds according to the present invention having antimicrobial activity are preferably used in the treatment or prevention of infectious diseases. Accordingly, according to a further aspect of the present invention, there is provided a method for treating or preventing an infectious disease, comprising administering an effective amount of a compound represented by formula (I) or its pharmacologically acceptable salt or their solvates to an animal including human. The term "treatment" as used herein means ameliorating an established disease state, and the term "prevention" as used herein means preventing the establishment of a disease state in the future.

The compounds according to the present invention can be applied to bacteria causative of various infectious diseases. Bacteria causative of infectious diseases include, for example, *Staphylococcus aureus*, *Staphylococcus epidermidis*, *Entercoccus*, *Escherichia coli*, *Pseudomonas aeruginosa*, *Bacillus subtilis*, *Salmonella*, or *Acinetobacter*. Preferred is *Staphylococcus aureus*, *Escherichia coli*, or *Pseudomonas aeruginosa*.

When the compound represented by formula (I) is 2-hydroxykanamycin B, the bacteria causative of infectious diseases are preferably *Staphylococcus aureus*, *Staphylococcus epidermidis*, *Entercoccus*, *Escherichia coli*, *Pseudomonas aeruginosa*, *Bacillus subtilis*, *Salmonella*, or *Acinetobacter*, more preferably *Staphylococcus aureus*, *Staphylococcus epidermidis*, *Entercoccus*, *Escherichia coli*, *Bacillus subtilis*, *Salmonella*, or *Acinetobacter*, still more preferably *Staphylococcus aureus*, *Staphylococcus epidermidis*, *Escherichia coli*, *Bacillus subtilis*, *Salmonella*, or *Acinetobacter*.

When the compound represented by formula (I) is 2-hydroxykanamycin C, the bacteria causative of infectious diseases are preferably *Staphylococcus aureus*, *Staphylococcus epidermidis*, *Escherichia coli*, *Bacillus subtilis*, *Salmonella*, or *Acinetobacter*, more preferably *Staphylococcus epidermidis*, *Escherichia coli*, *Bacillus subtilis*, *Salmonella*, or *Acinetobacter*, still more preferably *Staphylococcus epidermidis*, *Bacillus subtilis*, *Salmonella*, or *Acinetobacter*.

The effective dose of the compound according to the present invention may be properly determined by physicians in consideration of particular conditions, for example, the age, weight, type and severity of patients, and administration route. When the compound is orally administered to human, for example, the compound can be administered, for example, at a dose of 0.01 to 1000 mg/kg per adult per day. On the other hand, when the compound is intravenously administered, the compound can be administered at a dose of 0.001 to 100 mg/kg per adult per day.

EXAMPLES

The present invention is further illustrated by the following Examples that are not intended as a limitation of the invention.

In the following Examples, LC/MS analyses were carried out under the following conditions.

Conditions for LC/MS Analyses
(HPLC part: Waters 2690)
Column: Capcell Pak C18 MG, 4.6×150 mm, 5 μm (manufactured by Shiseido Company, Limited)
Mobile phase:
A: 0.2% Aqueous pentafluoropropionic acid solution
B: Acetonitrile
C: $H_2O$
Liner gradient: 0 min (A/B/C=10/10/80)→15 min (A/B/C=10/30/60)
Flow rate: 0.4 ml/min, temp.: 30° C.
(MS part: Waters ZQ) ESI method
Ion source temp.: 100° C.
Desolvation temp.: 380° C.
Desolvation gas flow: 350 L/hr
Cone gas flow: 50 L/hr
Capillary voltage: 3.5 kV
Cone voltage: positive: 30 V Example 1

Construction of Plasmid pDDOI for Introduction of 2-deoxy-scyllo-inosose Synthase Gene (orf11) Mutation of *Streptomyces kanamyceticus*

Regarding 2-deoxy-scyllo-inosose synthase (SEQ ID No. 1), aspartic acid at position 136 conserved as an amino acid residue important to binding to a substrate, glucose-6-phosphoric acid, was changed to asparagine to inactivate enzyme protein. Preparation was carried out by a PCR reaction using pKM9 (see Japanese Patent Application Laid-Open No. 173537/2004, Example 2, FERM P-19117) as a template.

A kanamycin biosynthetic cluster region utilized is shown in SEQ ID No. 2.

The following primers, i.e., a primer including Hind III or Xba I digestion site and a primer which had been designed so that aspartic acid (GAT) at position 136 from an initiation codon of a DOI synthase gene is mutated to asparagine (AAC), were used.

```
Km-Mu-Hind III
5'-GGGAAGCTTGACCTTGGAGGTATGTGT-3'    (SEQ ID No. 3)

Km-Mu-L
5'-GTTCAGCATGGCCACCACGGTGGT-3'       (SEQ ID No. 4)
```

(The underlined part represents mutation introduced part)

```
Km-Mu-R
5'-TCGGTGCTCTCGCTCAAGCAG-3'          (SEQ ID No.: 5)

Km-Mu-Xba I
5'-GGGTCTAGATGCCGTCCTGGTGGTAGT-3'    (SEQ ID No.: 6)
```

A PCR reaction was carried out using a primer combination of Km-Mu-Hind III (SEQ ID No. 3) with Km-Mu-L (SEQ ID No. 4) and a primer combination of Km-Mu-R (SEQ ID No. 5) with Km-Mu-Xba I (SEQ ID No. 6). The reaction was carried out using about 1 μg of genomic DNA, 0.3 μM of each primer, and KOD plus DNA polymerase (manufactured by TOYOBO CO., LTD.) under conditions of 94° C./2 min (94° C./15 sec, 50° C./30 sec, and 68° C./1.5 min)×25 cycles. As a result, about 1.5 kbp DNA fragments were specifically amplified. The DNA fragments were purified by a QIAquick PCR purification kit (manufactured by QIAGEN K.K.). The blunt end was phosphorylated (manufactured by NIPPON GENE CO., LTD.), and the phosphorylated DNA fragments were digested with Hind III and Xba I, followed by cloning into Hind III and Xba I sites of pUC119. The base sequence of the cloned DNA fragments were analyzed. As a result, it could be confirmed that the DNA fragments contained a 2-deoxy-scyllo-inosose synthase (orf11) gene (SEQ ID No. 7) with contemplated substitution by asparagine inserted thereinto.

Plasmid pSET152 (Bierman, M. et al., "Gene", (Netherlands), 1992, Vol. 116, p. 43-49) for conjugation transfer of *Actinomyces* was digested with Sph I and was blunted with T4 DNA polymerase. A Hind III linker (manufactured by TAKARA SHUZO CO., LTD.) was then linked thereto to construct pSET153. An about 2.8 kbp Hind III-Xba I fragment derived from pSET153 was linked to an about 3 kbp Hind III-Xba I fragments containing the gene subjected to amino acid substitution to obtain plasmid pDDOI for orf11 gene mutation introduction that had a conjugation transfer ability.

Example 2

Creation of Deoxystreptamine-Non-Producing Strain by Plasmid pDDOI for orf11 Gene Mutation Introduction

*Streptomyces kanamyceticus* which is a kanamycin producing bacterium was coated onto an MS agar medium (2% S soybean meal, 2% mannitol, 2% agar) and was cultivated at 28° C. for 3 days. After the cultivation, hyphae were scraped with 3 ml of 20% glycerol and were collected to prepare a hypha liquid of a host.

On the other hand, the *E. coli* (*Escherichia coli*) ET12567/pUZ8002 strain carrying plasmid pDDOI was inoculated into 100 ml of an LB liquid medium (1% Difco Bacto tryptone, 0.5% Difco yeast extract, 0.5% NaCl, and 0.1% glucose) containing 25 μg/ml of chloramphenicol, 25 μg/ml of kanamycin, and 50 μg/ml of apramycin and was cultivated at 37° C. overnight to prepare a preculture. The culture was inoculated into the same liquid medium as the precultivation so that the final concentration of the preculture was 1%, followed by cultivation at 37° C. for about 4 hr. The culture was washed twice with an LB liquid medium and was finally suspended in 10 ml of an LB liquid medium to prepare an *E. coli* liquid.

The hypha liquid of the host (500 μl) prepared above and 500 μl of the *E. coli* liquid were mixed together for harvesting. The harvested bacteria were then coated on an $MgCl_2$-added MS agar medium so that the final concentration of the bacteria was 10 mM. After cultivation at 28° C. for 20 hr, 1 ml of sterilized water containing 1 mg of apramycin and 1.5 mg of nalidixic acid was overlayered, and the cultivation was continued at 28° C. for 5 days to obtain an apramycin-resistant strain.

A genomic DNA was prepared from the apramycin-resistance strain with a MagExtractor genomic DNA extractor (manufactured by TOYOBO CO., LTD.) according to a protocol, and it was confirmed by PCR and an southern blot analysis that pDDOI was inserted into the chromosome by homologous recombination.

The homologous recombinant was inoculated into a modified YEME medium (50 ml), followed by shake cultivation at 28° C. for 2 days, and 1 ml of the culture was further inoculated into a fresh modified YEME medium (50 ml) to perform successive cultivation. This procedure was repeated five times. Thereafter, the culture diluted to a suitable vial cell count was coated onto an MS agar medium, followed by cultivation at 28° C. for 4 days. The grown colony was replicated onto an MS agar medium containing 20 µg/ml of apramycin and onto an apramycin-free MS agar medium, and 18 apramycin-sensitive strains that cannot grow in the apramycin-containing medium were selected.

Genomic DNAs of the apramycin-sensitive strains were prepared, and a PCR reaction was carried out using a primer combination of Km33 (5'-CTTCGTGAATCCCCCTT-3': SEQ ID No. 8) with Km35 (5'-GCCCACCGCCTCGATCA-3': SEQ ID No. 9) to obtain about 3.5 kbp amplified DNA fragments. The base sequence of these amplified DNA fragments was analyzed. As a result, one strain was a mutant strain in which substitution by asparagines as designed was observed, and, for 17 strains, the base sequences remained unchanged.

In order to examine the productivity of kanamycin, these strains were inoculated into 30 ml of a liquid growing medium (Umezawa, H. et al., "The Journal of Antibiotics", (Japan), 1977, Vol. 30, p. 181-188) prepared in a 250 ml-volume conical flask, followed by cultivation at 28° C. for two days. Thereafter, 1 ml of the culture was inoculated in 30 ml of a liquid producing medium (in which the amount of starch was increased from 1.2% to 6%), and shake cultivation was carried out at 26° C. for 7 days. In order to analyze the product, the culture was adjusted to pH 2.5 with 50% $H_2SO_4$, was placed in a 1.5-ml Eppendorf tube, and was centrifuged under conditions of 17,400×g and 10 min, and the supernatant was subjected to an LC/MS analysis. As a result, for one orf11 mutation introduced strain, the production of kanamycins was not observed, and 17 strains returned to the same base sequence as the parent strain produced kanamycin A (retention time 8.2 min, m/z 485) and kanamycin B (retention time 10.4 min, m/z 484).

Next, the kanamycin non-producing strain was coated onto an agar medium prepared by adding deoxystreptamine to the liquid medium, diluted to a half concentration, so as to give a concentration of 200 µg/ml, followed by cultivation at 28° C. for 7 days. Thereafter, the agar was frozen and thawed to extract the product which was then bioassayed. The assay bacterium was Bacillus subtilis ATCC6633. As a result, the product obtained by deoxystreptamine-free cultivation did not have antimicrobial activity, whereas, for the product obtained by deoxystreptamine-added cultivation, an inhibition circle indicating antimicrobial activity was detected. Accordingly, the product obtained by deoxystreptamine-added cultivation was subjected to an LC/MS analysis. As a result, kanamycin A and kanamycin B could be detected from the product. Thus, it was confirmed that the substitution of amino acid at position 136 of orf11 created a deoxystreptamine-dependent kanamycin producing strain, S. Kanamyceticus-DOS.

Example 3

Streptamine-Added Cultivation Utilizing Deoxystreptamine-Dependent Kanamycin Producing Strain The deoxystreptamine-dependent kanamycin producing strain obtained in Example 2 was cultivated in the liquid producing medium at 26° C. for 7 days. On the second and third days, streptamine adjusted so as to have a final concentration of 2,000 µg/ml was added.

Radio Light #800 was added to 2,000 L of the culture, and the mixture was filtered. The filtrate was adsorbed on 50 ml-volume Amberlite FPC3500 ($NH_4^+$ type, Rohm and Haas Japan K.K.). The resin was washed with water, and elution was then carried out with 0.5 N aqueous ammonia. The eluate was adjusted to pH 6 and was adsorbed on 50 ml-volume Dowex 50W ($NH_4^+$ type, Muromachi Technos CO., LTD.), and elution was carried out with 0.04 N to 0.2 N aqueous ammonia to obtain 57.6 mg of 2-hydroxykanamycin A, 32.8 mg of 2-hydroxykanamycin B, and 513.2 mg of 2-hydroxykanamycin C. The structures of these hydrokykanamycins were determined by an HR-FAB/MS (JEOL JMS-700, JEOL Ltd.) and NMR (JEOL JNM-LA400, JEOL Ltd.) spectral analysis.

Example 4

Myo-Inositol-Added Cultivation Utilizing Deoxystreptamine-Dependent Kanamycin Producing Strain The deoxystreptamine-dependent kanamycin producing strain obtained in Example 2 was coated onto the agar medium to which myo-inositol had been added to a concentration of 500 µg/ml, followed by cultivation at 28° C. for 7 days. Thereafter, the agar was frozen and thawed to extract the product which was then subjected to an LC/MS analysis. As a result, a peak attributable to 2-hydroxykanamycin C (retention time 8.3 min, m/z 501) was detected.

Example 5

Streptamine or Myo-Inositol-Added Cultivation in Kanamycin Producing Bacteria

In kanamycin producing bacteria (Streptomycin kanamyceticus), agar cultivation with the addition of 500 µg/ml of streptamine or myo-inositol was carried out in the same manner as in Example 4. The product was analyzed by LC/MS. As a result, in both the addition of streptamine and the addition of myo-inositol, it was detected that, in addition to kanamycin A (retention time 8.2 min, m/z 485) and kanamycin B (retention time 10.4 min, m/z 484), 2-hydroxykanamycin B (retention time 10.7 min, m/z 500) and 2-hydroxykanamycin C (retention time 8.3 min, m/z 501) were produced.

Example 6

Confirmation of Physicochemical Properties of Hydroxykanamycins B and C

The physicochemical properties of hydroxykanamycins B and C acquired in Examples 3 to 5 were examined and were found to be as follows.

Physicochemical Properties of 2-hydroxykanamycin B
(1) Color and properties: Colorless powder
(2) Molecular formula: $C_{18}H_{37}N_5O_{11}$
(3) Mass spectrum (HR-FAB/MS): measured value 500.2563 $(M+H)^+$, calculated value 500.2568
(4) Specific rotation: $[\alpha]D^{25}=+127.1°$ (c=1, $H_2O$)
(5) Ultraviolet absorption spectrum λmax nm: terminal adsorption ($H_2O$)

(6) Infrared absorption spectrum νmax cm$^{-1}$ (KBr): 3351, 2910, 1585, 1477, 1368, 1032

(7) $^1$H-NMR spectrum (400 MHz, D$_2$O) δ (ppm): 2.87 (1H, dd, H-1), 3.14 (1H, dd, H-2), 2.84 (1H, dd, H-3), 3.40 (1H, dd, H-4), 3.77 (1H, dd, H-5), 3.32 (1H, dd, H-6), 5.37 (1H, d, H-1'), 2.79 (1H, dd, H-2'), 3.58 (1H, dd, H-3'), 3.32 (1H, dd, H-4'), 3.81 (1H, m, H-5'), 2.84 (1H, dd, H-6'a), 3.06 (1H, m, H-6'b), 5.05 (1H, d, H-1''), 3.52 (1H, dd, H-2''), 3.02 (1H, dd, H-3''), 3.35 (1H, dd, H-4''), 3.93 (1H, dt, H-5''), 3.78 (2H, br d, H-6'')

[TSP=0 ppm]

(8) $^{13}$C-NMR spectrum (100 MHz, D$_2$O) δ (ppm): 57.0 (d, C-1), 73.5 (d, C-2), 55.7 (d, C-3), 82.9 (d, C-4), 74.7 (d, C-5), 84.7 (d, C-6), 100.7 (d, C-1'), 55.9 (d, C-2'), 74.1 (d, C-3'), 72.0 (d, C-4'), 73.3 (d, C-5'), 42.1 (t, C-6'), 100.7 (d, C-1''), 72.4 (d, C-2''), 54.9 (d, C-3''), 69.8 (d, C-4''), 72.7 (d, C-5''), 60.9 (t, C-6'')

[Dioxane=67.4 ppm]

(9) Solubility: soluble in water, and insoluble in ethyl acetate and chloroform

Physicochemical Properties of 2-hydroxykanamycin C (1) Color and properties: Colorless powder (2) Molecular formula: C$_{18}$H$_{36}$N$_4$O$_{12}$ (3) Mass spectrum (HR-FAB/MS): measured value 501.2398 (M+H)$^+$, calculated value 501.2408

(4) Specific rotation: $[\alpha]D^{25}$=+114.3° (c=1, H$_2$O)

(5) Ultraviolet absorption spectrum λmax nm: terminal absorption (H$_2$O)

(6) Infrared absorption spectrum νmax cm$^{-1}$ (KBr): 3358, 2920, 1591, 1457, 1369, 1032

(7) $^1$H-NMR spectrum (400 MHz, D$_2$O) δ (ppm): 2.88 (1H, dd, H-1), 3.14 (1H, dd, H-2), 2.83 (1H, dd, H-3), 3.39 (1H, dd, H-4), 3.76 (1H, dd, H-5), 3.33 (1H, dd, H-6), 5.32 (1H, d, H-1'), 2.81 (1H, dd, H-2'), 3.60 (1H, dd, H-3'), 3.41 (1H, dd, H-4'), 3.86 (1H, m, H-5'), 3.76 (1H, dd, H-6'a), 3.88 (1H, m, H-6'b), 5.06 (1H, d, H-1''), 3.54 (1H, dd, H-2''), 3.04 (1H, dd, H-3''), 3.37 (1H, dd, H-4''), 3.94 (1H, dt, H-5''), 3.79 (2H, br d, H-6'')

[TSP=0 ppm]

(8) $^{13}$C-NMR spectrum (100 MHz, D$_2$O) δ (ppm): 57.1 (d, C-1), 73.5 (d, C-2), 56.0 (d, C-3), 83.6 (d, C-4), 74.8 (d, C-5), 84.8 (d, C-6), 101.1 (d, C-1'), 56.1 (d, C-2'), 74.3 (d, C-3'), 70.6 (d, C-4'), 73.7 (d, C-5'), 61.4 (t, C-6'), 100.9 (d, C-1''), 72.4 (d, C-2''), 55.1 (d, C-3''), 69.7 (d, C-4''), 72.8 (d, C-5''), 60.9 (t, C-6'')

[Dioxane=67.4 ppm]

(9) Solubility: soluble in water, and insoluble in ethyl acetate and chloroform

Test Example 1

Antimicrobial Activity of 2-hydroxykanamycin B and 2-hydroxykanamycin C

The antimicrobial activity of 2-hydroxykanamycin B and 2-hydroxykanamycin C was measured as the minimum inhibitory concentration (MIC) by an agar dilution method. Test bacteria which had been cultivated overnight in a growth medium were adjusted to 10$^6$ cells/ml, and one platinum loop thereof was inoculated in a Mueller-Hinton agar medium containing 2-hydroxykanamycin B or 2-hydroxykanamycin C (manufactured by Difco Laboratories Inc.), followed by cultivation at 37° C. for 18 to 20 hr.

The results are shown in Table 1.

TABLE 1

Antimicrobial activity of 2-hydroxykanamycins B and C

| Strain | MIC (μg/mL) | |
| --- | --- | --- |
| | 2-Hydroxykanamycin B | 2-Hydroxykanamycin C |
| Staphylococcus aureus ATCC29213 | 2 | 128 |
| Staphylococcus aureus 209P JC-1 | 2 | 128 |
| Staphylococcus epidermidis ATCC14990 | 1 | 32 |
| Bacillus subtilis ATCC6633 | 0.5 | 16 |
| Enterococcus faecalis ATCC29212 | 64 | >128 |
| Enterococcus faecium ATCC19434 | 64 | >128 |
| Salmonella typhimurium ATCC13311 | 1 | 32 |
| Acinetobacter calcoaceticus ATCC23055 | 1 | 32 |
| Escherichia coli ATCC25922 | 4 | 128 |
| Pseudomonas aeruginosa PA01 | 128 | >128 |

---

The invention claimed is:

1. A compound represented by formula (I) or its pharmacologically acceptable salt:

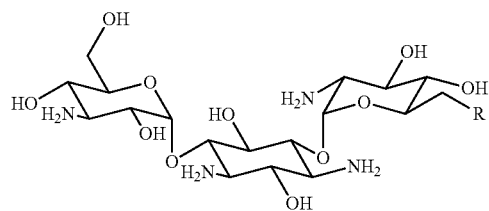

wherein R represents amino or hydroxyl.

2. A process for producing a compound represented by formula (I):

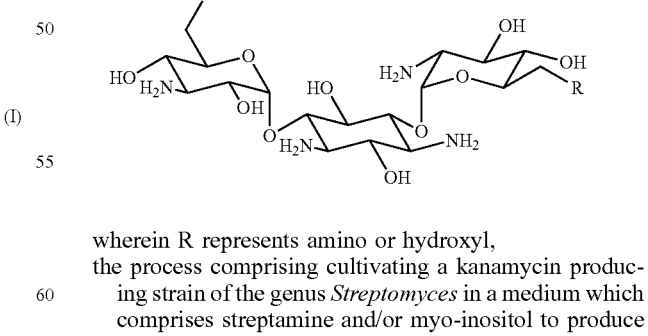

wherein R represents amino or hydroxyl,
the process comprising cultivating a kanamycin producing strain of the genus *Streptomyces* in a medium which comprises streptamine and/or myo-inositol to produce the compound.

3. The process according to claim 2, wherein 2-deoxy-scyllo-inosose synthase in the kanamycin producing strain has been inactivated.

4. The process according to claim 3, wherein the strain is *S. Kanamyceticus*-DOS.

5. The process according to claim 3, wherein the kanamycin producing strain is 2-deoxystreptamine-dependent.

6. The process according to claim 3, wherein the medium comprises streptamine.

7. The process according to claim 6, wherein the compound represented by formula (I) is produced together with 2-hydroxykanamycin A.

8. The process according to claim 3, wherein the medium comprises myo-inositol.

9. The process according to claim 8, wherein R represents hydroxyl.

10. The process according to claim 3, wherein the kanamycin producing strain has integrated therein a gene that codes for a polypeptide selected from the following polypeptides (a) to (d):
   (a) a polypeptide consisting of an amino acid sequence represented by SEQ ID No. 1 having a mutation in which aspartic acid at position 136 has been changed to asparagine,
   (b) a polypeptide consisting of the amino acid sequence defined in (a) in which one or more amino acids have been substituted, deleted, added, or inserted, the polypeptide having an activity functionally equivalent to the polypeptide defined in (a), and
   (c) a polypeptide consisting of an amino acid sequence having 80% or more homology with the amino acid sequence defined in (a), the polypeptide having an activity functionally equivalent to the polypeptide defined in (a).

11. The process according to claim 10, wherein the polypeptide defined in (b) or (c) holds the mutation defined in (a).

12. The process according to claim 10, wherein the one or more amino acids in (b) is 1 to 40 amino acids.

13. The process according to claim 10, wherein the homology in (c) is not less than 90%.

* * * * *

SEQUENCE LISTING

<160> NUMBER OF SEQ ID NOS: 9

<210> SEQ ID NO 1
<211> LENGTH: 390
<212> TYPE: PRT
<213> ORGANISM: Streptomyces kanamyceticus

<400> SEQUENCE: 1

```
Met Gln Val Thr Thr Ile Thr Met Asp Asp Val Gln Tyr Pro Tyr Arg
1               5                   10                  15

Leu Gly Thr Asp Cys Leu Asp Gly Ile Val Thr Arg Leu Gly Glu Leu
            20                  25                  30

Gly Ala Ser Arg Tyr Leu Ile Val Ser Asp Pro Arg Val Ala Glu Leu
        35                  40                  45

Tyr Gly Gln Gly Leu Arg Glu Arg Leu Ala Glu Gln Ala Gly Pro Ala
```

```
            50                  55                  60
Glu Leu Ile Thr His Ala Ser Gly Glu Gln Asn Lys Gly Leu Pro Ala
 65                  70                  75                  80

Leu His Asp Leu Ala Glu Glu Ala Leu Arg Arg Gly Ala Asp Arg Gln
                 85                  90                  95

Ser Ile Val Val Ala Leu Gly Gly Val Thr Gly Asn Ile Ala Gly
                100                 105                 110

Leu Leu Ala Ala Leu Leu Phe Arg Gly Ile Arg Leu Val His Val Pro
                115                 120                 125

Thr Thr Val Val Ala Met Leu Asp Ser Val Leu Ser Leu Lys Gln Ala
            130                 135                 140

Val Asn Ala Gly Val Gly Lys Asn Leu Val Gly Thr Phe Tyr Gln Pro
145                 150                 155                 160

Val Glu Val Leu Ala Asp Thr Ala Met Leu Arg Thr Leu Pro Val Arg
                165                 170                 175

Glu Val Arg Ser Gly Met Cys Glu Val Val Lys Asn Ser Leu Ala Ile
                180                 185                 190

Arg Pro Ser Met Ile Asp Gln Leu Ser Ala Gly Leu Arg Pro Asp Gly
            195                 200                 205

Arg Tyr Pro Asp Asp Thr Met His Trp Ile Ile Glu Ser Leu Ala
210                 215                 220

Ala Lys Ala Gln Val Thr Ala Tyr Asp Lys Tyr Glu Arg Gly Glu Gly
225                 230                 235                 240

Leu Ile Leu Glu Tyr Gly His Thr Val Gly His Ala Val Glu His Ser
                245                 250                 255

Ser Gln Gly Ala Val Pro His Gly Ala Ala Val Ala Leu Gly Met Ile
            260                 265                 270

Ala Ala Ala Gln Val Ser His Arg Ala Gly Trp Ala Ser Ala Glu Leu
            275                 280                 285

Val Asp Leu His Arg Glu Leu Val Ala Lys Thr Gly Val Ala Arg Arg
290                 295                 300

Ile Pro Ser Asp Ile Pro Leu Ser Ala Val Arg His Arg Leu Ser Phe
305                 310                 315                 320

Asp Asn Lys Arg Gly Tyr Leu Pro Ala Ser Ala Asp Thr Tyr Pro Met
                325                 330                 335

Val Leu Leu Glu Ser Pro Gly Lys Val Leu Arg Ser Glu Gly Thr Val
            340                 345                 350

Leu Thr Ala Ala Pro Arg Asp Leu Val Asp Ala Val Val Asp Glu Leu
            355                 360                 365

Ala Glu Pro Pro Arg Pro Ala Ala Ala Arg Thr Asp Asp Ala Ala Thr
            370                 375                 380

Val Leu Gly Gly Ala Gly
385                 390

<210> SEQ ID NO 2
<211> LENGTH: 5261
<212> TYPE: DNA
<213> ORGANISM: Streptomyces kanamyceticus

<400> SEQUENCE: 2
gtgcgcatca tctccgtaca ggaggcggcc acccgcacct tcgacgtctg cgtggtgggc      60
agcggcgcct ccggtgccat caccgccgcg gtgctcgccg aacggggcct gtccgtgctc     120
atcctcgaac agggcaccgc gatcccgccg ggcaccgacc acgacgacgt cgaggacccc     180
```

```
gacacctggg cgtacgcacg cgacggggaa ggctggagca aggagggcta tccctggagc    240
gccatggcgt tcggcggcgg cacggtgttc tacggcggca tctccttccg ctacgaacag    300
cgcgacctcg acccgccgcc cgcgctcctc ggcgacgccg actacgcgca ctggcggctg    360
cggctcgacg aactggagcc gcactacgac tgggtggagg accggctcgg cgtgagcggc    420
ccgtcccacg gccgggtggg cgactacgcc ttcccccact acgcgcgggg ctcgctgccg    480
cacaccccga tgggcggcgc gctggcccgg ggcgccgacg ccctgggggct gaccccgctg    540 tccaccccga tggcgatcag cggggccagg gaccggcacg gccccggctg cgccgagctg    600
acgccgtgca ccggcttcac ctgcccggtc aacgccaagg ccgatgtgat cagccgcatc    660
ctggcgcgcg ccgagggggga cgtgtccgtc gccctggaca ccagagcggt gcggttcgtg    720
gcctcggcac cggggcgggc gaaacgtctc gaagtgctcg gcggcagtcc ccgcagccgc    780
cgctcggtcc atgccgaccg cttcgtcctc gcggccaacg ccatccagtc cgccgcgctc    840
ctgctgcgtt cggcggaccg gcgcgagccg acggcatgg ggaactccag cggtcaggtg    900
ggccgccacc tggccatgaa gaacagcgtc tacgtccgcg gcaggaccca ggagcggatc    960
gtcgcccacc agccgctgcg ccatcgctac tccagcgtct gcgtcctgga ccacctgcgc    1020
ggtgcggagt tcccccgggca gctgggcggg atcatctacg aggccaaccc gtgggaggac    1080
cccgaggccg accgtcctgg cgccggttcg ctgctccagc tggagtgcct cctcggcgac    1140
cgcccgcagg cccgcaacat ggtgcggctc gccaggagcc gggaccggga cgggctccag    1200
cgcatcgtca tggactaccg ccagcacccc ttggacggcg aacgcctgga cgtgctccag    1260
gggaaggcga aggatgtact gcacgcgcc ggggccgagc gcaccgagtc cgtcgacagc    1320
gatttcgcga ccggcagcac gcatctgcac ggcacgctgc gcgccggtga cgaccccgcg    1380
acctcggtga ccgaccggac gggccggctg cacgactacg acaacgtgtg gtcggcggac    1440
ggcgcgacgt tccccttcgc cgggaacttc aatcccaccc tcaccatcca ggccaatgcc    1500
cggcggatcg cggtcggcat ctcctgacgg ccgcccccct ccccctcccc cgtacgccct    1560 gccgccttc cccgtggcga gccaccccct tcgtgaatcc cccttcgtga cgcgcgaact    1620
gtcttcgacc ttggaggtat gtgtcatgcc cctgcaaagt tcacggcttg cggtcgacaa    1680
cggaaccccc gtccgcggca agccctggcc ggtgtggccg cagcccaccg acggcaccct    1740
cgacgccctc tcccgcgtcc tgcgttccgg ccgctgggcc atcagcggcc cctaccgggg    1800
cgtggagtcg gccgaacgcc gcttcgcccg ccggttcgcc gactaccacc gcatcgccca    1860
ctgcgtgccc gcctccagcg gtacggcgag cctgatgctg gccctggagg cctgtggcgt    1920
cggcgcggga gacgaggtca tcctgcccgg cgtcacctgg gtcgcctccg cctccacggt    1980
ggtgggcgtc aacgcggtgc cggtgttcgc cgacatcgac ccggacaccc tctgcctcga    2040
cccggacgcc gtcgaggcgg ccatcacccc ggccaccaag gcgatcgtcg tcgtccacct    2100
ctacgcggcc gtcgccgacc tcacccgcct caaggaggtg gccgaccggc acggcatcgt    2160
gctcatcgag gactgcgcgc aggccacggg cgccgagttc gaaggccaca aggtcggcac    2220
cttcggcgcg gtcggcacct tcagcatgca gcagagcaag gtcctgacca gcggcgaggg    2280
cggcgccgcc atcaccgccg acccggtgct cgcccgccgg atggaacacc tgcgcgcgga    2340
cggccgctgc taccgcgatc aggcgccgcc ctccggccac atggagctcg tcgagacggg    2400
cgagctgatg ggcagcaacc gctgcatctc cgagttccag gcagcggtcc tgaccgagca    2460
gctgggcgaa ctcgaccggt tcaacgccct gcgacggcac aacgcggaac tcctcgacgc    2520
gctgctgacc gacgtcggat accgcccgca gcgcagcacg cccggcacca ccgcccgcac    2580
```

```
gtactacacc tacgtcgccg agctgcccga cgcggaactg cccggcgcgg acatcaccaa    2640
ggtcaccgag gcgctgaccg ccgaactcgg cttcccggtg caccggcct actcgccgct     2700 caacgccaac cccctgtacg acccggccag tcgcagccgg ttcgccctcg gaccgcagca    2760
cgagaagctc atcgaccccg cccgattcgt gctcccggtg agcggccgcc tgacgcgtcg    2820
gctcgtcacc ttccaccacg ccgccctgct cggcgacgag tcggacatga gggacatcgc    2880
ggaagcgttc accaaggtgc tccagcaccg ggccgtcctg gccgcttgag ccgaagccgt    2940
cacacacgcc ttcaggattg gggacagacc atgcaggtca ccaccatcac gatggatgac    3000
gtccagtatc cctaccgatt aggcacggac tgcctcgacg catcgtcac cgcctcggc     3060 gaactcggcg ccagccgcta cctgatcgtc agcgacccca gggtcgccga gctgtacggg    3120
caggggctgc gcgaacggct cgcggagcag gcgggacccg ccgagctgat cacccatgcc    3180
tcgggagaac agaacaaggg cctgcccgca ctgcacgacc tggccgagga ggcgctgcgg    3240
cgcggcgccg accggcagag catcgtcgta gcactcggcg gcgtgtcac cgggaacatc     3300 gcggggctgc tggccgcgct gctcttccgc ggcatccgtc tggtgcacgt gcccaccacc    3360
gtggtggcca tgctggattc ggtgctctcg ctcaagcagg ccgtgaacgc gggagtcggc    3420
aagaacctgg tcggcacctt ctaccagccc gtcgaagtgc tcgccgacac cgcgatgctg    3480
cgcaccctgc cggtccgcga ggtcaggtcg gggatgtgcg aggtggtgaa gaactcgctc    3540
gccatccgcc ccagcatgat cgaccagctg tcggccgggc tgcgccccga cggccgctat    3600
cccgacgaca cgatgcactg gatcatctac gagagcctgg ccgccaaggc ccaggtcacg    3660
gcgtacgaca agtacgagcg cggcgaggga ctcatcctgg agtacgggca caccgtcggg    3720
cacgccgtgg agcactcctc gcagggagcc gtgccgcacg gcgccgccgt cgcgctcggc    3780
atgatcgccg ccgcccaggt ctcccaccgg gcgggctggg cctcggccga actcgtcgac    3840
ctgcaccggg agctcgtcgc caagaccggg gtcgcgcggc gcatcccgtc cgacataccg    3900
ctctccgccg tcaggcaccg cctctccttc gacaacaagc ggggctacct cccggcctcc    3960
gccgacacct atccgatggt gctgctcgaa tcccccggca aggtgctgcg cagcgagggc    4020
accgtcctga cggcggcgcc acgggacctg gtcgacgcgc tggtcgacga actcgcggaa    4080
cccccacggc ccgcggccgc gaggaccgac gacgccgcca ccgtcctcgg cggtgccggg    4140
tgagcgcccc cgtgcgcgtc ggcgtcgtcg gtgcggggtt catgggcggg gtgcacgccg    4200
aggtggtggc ggctcatccc ggcgcccggc tcgaagcggt gcacgacctc gaccccgccg    4260
ccgccaggga cctggccgag cggttccgcg ccgagcgggc cgagccctcc tgggcggacc    4320
tgctcgccga ccccgcgatc gacctgctca tcatcaccac gcccaacggg ctgcaccacc    4380
ggcaggcggc cgaggcgctg cggcggggca agcacgtact ggtggagaag ccgctcggtg    4440
tcacgccgga gcaggtggcc gagctcgtcg aactcgccgg acggcacgac cgggtccttg    4500
cccacggaag caacttcgtg cacagcccga agttcgtccg ggcccgtcaa ctggtcgcgg    4560
acaccgaggc gttcggacgg ccgcacctgg tccgggtcgt cttccgcaac tcgggccccg    4620
aggccgcctg ggccgcgtcc aaggacctcg cgggcggcgg agccctcctg gacctgggct    4680
gtcacgcggt ggagctgtgc cggtggctgc tcgacgcgc cgacgtcgag tcggtcagcg     4740
cccgactgca gcgggtgcgg ccgccccacg acgccgaagc ggaccgcgcg tccggcaccg    4800
cgggaaccgc gcgggtcgcg ctggaggacc aggcgctgct ggtcatggag ttcgccgacg    4860
gcgcggtcgg gcagtgcgac gtctcctggg tcacccaggg cggtgagcag gtcaccgcgg    4920
```

-continued

```
agatcatcgg caccaagggc agggtcgagg tcgacctgtg gaccggcatg gggctgcgcg    4980
cctactcgga caagggctat caggacgtct gggatcccga gcagggctgg gtgcatccgg    5040
aatgggagtg gatccgggcg agcggctact accaccagga cggcaccgtg atcgaggcgg    5100
tgggccaggg catcccctc acccacggcc ccgcggaagc gctcgcctcg gcccgtgtcc    5160
tggccaccgg ttaccgcagt cacgcggagg ggcgggtact gcggctgtcc ggcgcgccgg    5220
tcggccctgg cgcgtcgacg acggcggcgg gctcggaatg a    5261
```

<210> SEQ ID NO 3
<211> LENGTH: 27
<212> TYPE: DNA
<213> ORGANISM: Artificial Sequence
<220> FEATURE:
<223> OTHER INFORMATION: Synthetic construct; primer

<400> SEQUENCE: 3

```
gggaagcttg accttggagg tatgtgt                                         27
```

<210> SEQ ID NO 4
<211> LENGTH: 24
<212> TYPE: DNA
<213> ORGANISM: Artificial Sequence
<220> FEATURE:
<223> OTHER INFORMATION: Synthetic construct; primer

<400> SEQUENCE: 4

```
gttcagcatg gccaccacgg tggt                                            24
```

<210> SEQ ID NO 5
<211> LENGTH: 21
<212> TYPE: DNA
<213> ORGANISM: Artificial Sequence
<220> FEATURE:
<223> OTHER INFORMATION: Synthetic construct; primer

<400> SEQUENCE: 5

```
tcggtgctct cgctcaagca g                                               21
```

<210> SEQ ID NO 6
<211> LENGTH: 27
<212> TYPE: DNA
<213> ORGANISM: Artificial Sequence
<220> FEATURE:
<223> OTHER INFORMATION: Synthetic construct; primer

<400> SEQUENCE: 6

```
gggtctagat gccgtcctgg tggtagt                                         27
```

<210> SEQ ID NO 7
<211> LENGTH: 1176
<212> TYPE: DNA
<213> ORGANISM: Streptomyces kanamyceticus

<400> SEQUENCE: 7

```
atgcaggtca ccaccatcac gatggatgac gtccagtatc cctaccgatt aggcacggac     60
tgcctcgacg gcatcgtcac gcgcctcggc gaactcggcg ccagccgcta cctgatcgtc    120
agcgacccca gggtcgccga gctgtacggg caggggctgc gcgaacggct cgcggagcag    180
gcgggacccg ccgagctgat cacccatgcc tcgggagaac agaacaaggg cctgcccgca    240
ctgcacgacc tggccgagga ggcgctgcgg cgcggcgccg accggcagag catcgtcgta    300
gcactcggcg gcggtgtcac cgggaacatc gcggggctgc tggccgcgct gctcttccgc    360
```

```
ggcatccgtc tggtgcacgt gcccaccacc gtggtggcca tgctggattc ggtgctctcg      420
ctcaagcagg ccgtgaacgc gggagtcggc aagaacctgg tcggcacctt ctaccagccc      480
gtcgaagtgc tcgccgacac cgcgatgctg cgcaccctgc cggtccgcga ggtcaggtcg      540
gggatgtgcg aggtggtgaa gaactcgctc gccatccgcc ccagcatgat cgaccagctg      600
tcggccgggc tgcgccccga cggccgctat cccgacgaca cgatgcactg gatcatctac      660
gagagcctgg ccgccaaggc ccaggtcacg gcgtacgaca agtacgagcg cggcgaggga      720
ctcatcctgg agtacgggca caccgtcggg cacgccgtgg agcactcctc gcagggagcc      780
gtgccgcacg gcgccgccgt cgcgctcggc atgatcgccg ccgcccaggt ctcccaccgg      840
gcgggctggg cctcggccga actcgtcgac ctgcaccggg agctcgtcgc caagaccggg      900
gtcgcgcggc gcatcccgtc cgacataccg ctctccgccg tcaggcaccg cctctccttc      960
gacaacaagc ggggctacct cccggcctcc gccgacacct atccgatggt gctgctcgaa     1020
tcccccggca aggtgctgcg cagcgaggge accgtcctga cggcggcgcc acgggacctg     1080
gtcgacgcgg tggtcgacga actcgcggaa ccccacggc ccgcggccgc gaggaccgac      1140
gacgccgcca ccgtcctcgg cggtgccggg tgatga                                1176

<210> SEQ ID NO 8
<211> LENGTH: 17
<212> TYPE: DNA
<213> ORGANISM: Artificial sequence
<220> FEATURE:
<223> OTHER INFORMATION: Synthetic construct; primer

<400> SEQUENCE: 8
cttcgtgaat cccccctt                                                      17

<210> SEQ ID NO 9
<211> LENGTH: 17
<212> TYPE: DNA
<213> ORGANISM: Artificial Sequence
<220> FEATURE:
<223> OTHER INFORMATION: Synthetic construct; primer

<400> SEQUENCE: 9
gcccaccgcc tcgatca                                                       17
```